(12) United States Patent
Demirev et al.

(10) Patent No.: US 7,020,559 B1
(45) Date of Patent: Mar. 28, 2006

(54) METHODS FOR IDENTIFYING AND CLASSIFYING ORGANISMS BY MASS SPECTROMETRY AND DATABASE SEARCHING

(75) Inventors: Plamen A. Demirev, College Park, MD (US); Catherine Fenseleau, College Park, MD (US)

(73) Assignee: University of Maryland, College Park, MD (US)

( * ) Notice: Subject to any disclaimer, the term of this patent is extended or adjusted under 35 U.S.C. 154(b) by 0 days.

(21) Appl. No.: 09/856,044

(22) PCT Filed: Nov. 17, 1999

(86) PCT No.: PCT/US99/27191

§ 371 (c)(1),
(2), (4) Date: Aug. 3, 2001

(87) PCT Pub. No.: WO00/29987

PCT Pub. Date: May 25, 2000

Related U.S. Application Data

(60) Provisional application No. 60/108,696, filed on Nov. 17, 1998, provisional application No. 60/120,679, filed on Feb. 19, 1999.

(51) Int. Cl.
*G01N 33/48* (2006.01)

(52) U.S. Cl. .......................................... 702/19; 702/20
(58) Field of Classification Search .................. 436/89, 436/94; 435/173, 7, 23, 377, 6, 5; 422/102; 702/19, 20
See application file for complete search history.

(56) References Cited

U.S. PATENT DOCUMENTS

| 5,101,105 A | 3/1992 | Fenselau et al. |
| 5,538,897 A * | 7/1996 | Yates et al. .................... 436/89 |
| 5,572,025 A | 11/1996 | Cotter et al. |
| 5,696,376 A | 12/1997 | Doroshenko et al. |

(Continued)

FOREIGN PATENT DOCUMENTS

WO          WO 95/25281          9/1995

(Continued)

OTHER PUBLICATIONS

Wang et al., "Investigation of Spectral Reproducibility in Direct Analysis of Bateria Proteins by Matrix-assisted Laser Desorption/Ionization Time-of-flight Mass Spectrometry", Apr. 30, 1998, Rapid Communications in Mass Spectrometry, vol. 12, pp. 456-464.*

(Continued)

*Primary Examiner*—Ardin H. Marschel
*Assistant Examiner*—Jerry Lin
(74) *Attorney, Agent, or Firm*—Millen, White, Zelano & Branigan, P.C.

(57) ABSTRACT

A method for rapid identification of biological materials is presented, which exploits the wealth of information contained in genome and protein sequence databases (5). In a preferred embodiment, the method utilizes the masses of a set of ions by MALDI TOF mass spectrometry of intact or treated cells (1). Subsequent correlation (4) of each ion in the set to a protein, along with the organismic source of the protein, is performed by searching a database comprising protein molecular weights (9).

13 Claims, 8 Drawing Sheets

U.S. PATENT DOCUMENTS

| | | | |
|---|---|---|---|
| 5,809,212 | A | 9/1998 | Shasha |
| 5,869,240 | A | 2/1999 | Patterson |
| 5,930,784 | A | 7/1999 | Hendrickson |
| 5,930,803 | A | 7/1999 | Becker et al. |
| 5,977,890 | A | 11/1999 | Rigoutsos et al. |
| 5,986,652 | A | 11/1999 | Medl et al. |
| 5,987,470 | A | 11/1999 | Meyers et al. |

FOREIGN PATENT DOCUMENTS

| | | |
|---|---|---|
| WO | WO 98/09314 | 3/1998 |

OTHER PUBLICATIONS

Mann et al., "Use of Mass Spectrometric Molecular Weight Information to identify Proteins in Sequence Databases," Biological Mass Spectrometry, vol. 22, No. 6 (1993) pp. 338-345.*

Yates III, "Mass Spectrometry and the Age of the Proteome," Journal of Mass Spectrometry. vol. 33, 1-19 (1998).*

Fernando J. Pineda et al., "Testing the Significance of Microorganism identification by Mass Spectrometry and Proteome Database Search", Anal. Chem., vol. 72, pp. 3739-3744 (2000).

Yuqin Dai et al., "Two-layer Sample Preparation: A method for MALDI-MS Analysis of Complex Peptide and Protein Mixtures", Anal. Chem., vol. 71, pp. 1087-1091 (1999).

R. A. Van Bogelen et al., "*Escherichia coli* Proteome Analysis Using the Gene-Protein Database", Electrophoresis, vol. 18, pp. 1243-1251 (1997).

J. D. Cavalcoli et al., "Unique Identification of Proteins from Small Genome Organisms: Theoretical Feasibility of High Throughput Proteome Analysis", Electrophoresis, vol. 18, pp. 2703-2708 (1997).

T. Krishnamurthy et al., "Rapid Identification of Bacteria by Direct Matrix-Assisted Laser Desorption/Ionization Mass Spectrometric Analysis of Whole Cells", Univ. of Washington School of Medicine.

X. Liang et al., "Determination of Baterial Protein Profiles by Matrix-Assisted Laser Desorption/Ionization Mass Spectrometry with . . . ", Rapid Comm. in Mass Spectrometry, vol. 10, pp. 1219-1226 (1996).

I. Humphrey-Smith et al., "Proteome Analysis: Genomics via the Output Rather than the Input Code", Journal of Protein Chemistry, vol. 16, No. 5, pp. 537-544 (1997).

John R. Yates, III, "Mass Spectrometry and the Age of the Proteome", J. of Mass Spectrometry, vol. 33. pp. 1-19 (1998).

J. H. M. van Adrichem et al., "Investigation of protein patterns in mammaliam cells and culture supernatants by matrix-assisted laser desorption/ionization . . . ", Anal. Chem., vol. 70, pp. 923-930 (1998).

M. L. Easterling, "Monitoring Protein Expession in Whole Bacterial Cells with MALDI Time-of-Flight Mass Spectrometry", Anal. Chem., vol. 70, pp. 2704-2709 (1998).

S.J. Cordwell et al., "Proteome analysis of *Spiroplasma melliferum* (A56) and protein characterization across species boundaries", Electrophoresis, vol. 18, pp. 1335-1346 (1997).

Walter P. Blackstock et al., "Proteomics: Quantitative and Physical Mapping of Cellular Protein", TIBTECH, vol. 17, pp. 121-127 (1999).

Fred W. McLafferty et al., "Techview: Biochemistry, Biomoleculr Mass Spectrometry", SCIENCE, vol. 284, pp. 1289-1290 (1999).

* cited by examiner

METHODS FOR IDENTIFYING AND CLASSIFYING ORGANISMS BY MASS SPECTROMETRY AND DATABASE SEARCHING

CROSS-REFERENCE TO APPLICATIONS

This application claims the benefit of U.S. Provisional Application Nos. 60/108,696, filed Nov. 17, 1998, and 60/120,679, filed Feb. 19, 1999, which are hereby incorporated by reference in their entirety.

STATEMENT AS TO RIGHTS TO INVENTIONS MADE UNDER FEDERALLY SPONSORED RESEARCH AND DEVELOPMENT

The U.S. Government may have certain rights in these inventions pursuant to contract number MDA 97296 D0002 awarded by DARPA (Defense Advanced Research Projects Agency).

BACKGROUND OF THE INVENTION

The development of methods of rapidly identifying and characterizing biological materials, such as microorganisms and cells, is major focus of academic and industrial research. The need for such methods has been felt in the health, laboratory, and environmental industries. In medicine, for example, the exponential rise in antibiotic-resistant bacteria and emerging viral disease has caused a crisis in the healthcare and food industries. As a result, there has been a continued pressure to find new, reliable, and rapid means of characterizing pathological and disease-causing organisms. Similarly, the threats of biological warfare and terrorist activities which have been felt world-wide has caused an escalated search for ways of identifying putative biological agents, especially in the field, in airports, and in other public areas.

Coupled with the need for advanced biological agent detection methods has been an escalating effort in the sequencing of DNA from all types of organisms and identifying expressed genes. The complete genomic sequences of a number of microorganisms had been completed. The availability of such information about genome and proteome of whole organisms is an important reservoir to be exploited for identifying and characterizing unknown and known organisms.

DESCRIPTION OF THE INVENTION

Figure 1:
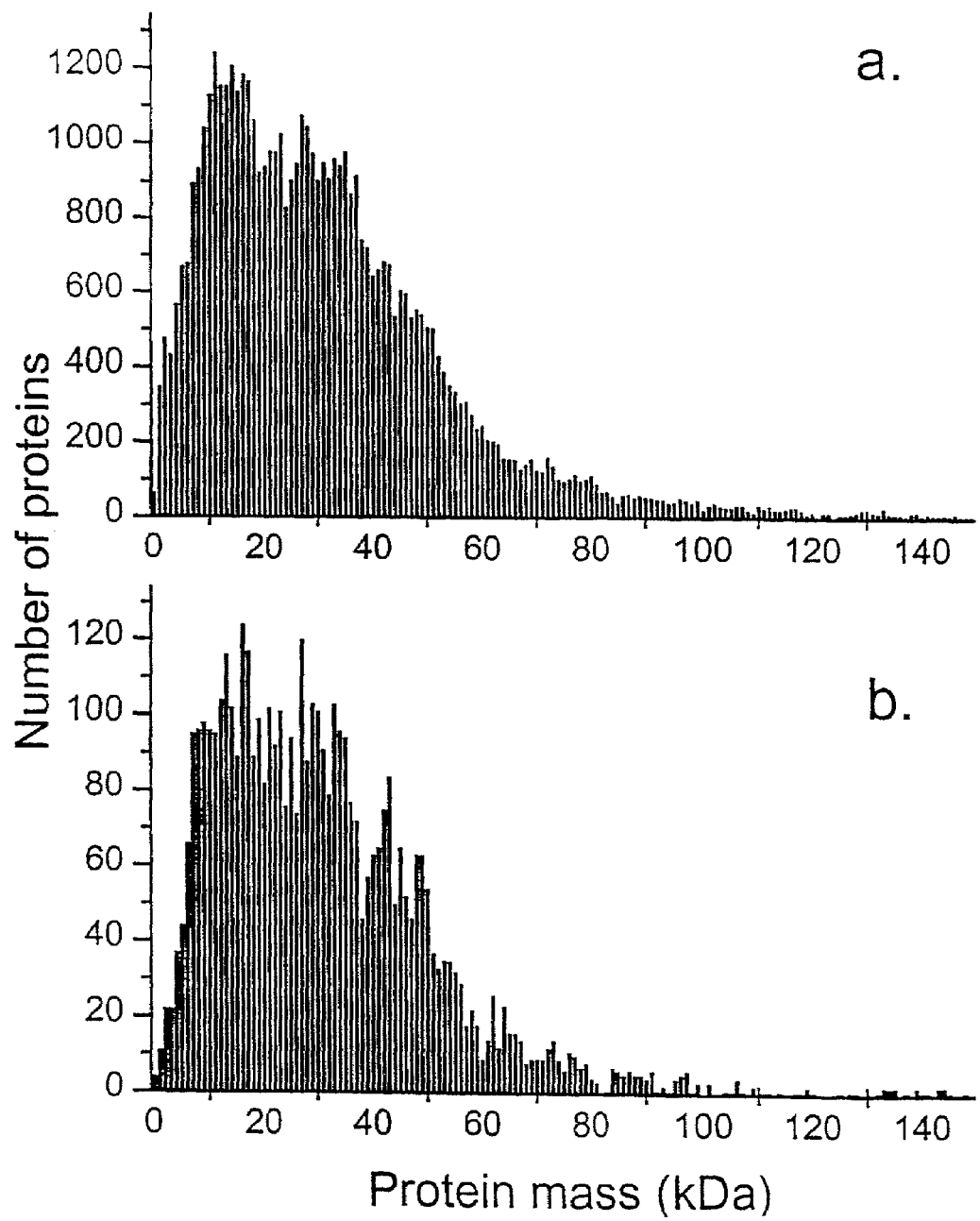
FIG. 1: Molecular mass distribution (in bins of 1 kDa) of proteins deposited in the SwissPROT/TrEMBL sequence database: a) all prokaryotic proteins, and b) all proteins from B. subtilis.

The present invention relates to compositions of matter, instruments, processes (e.g., as carried using computer software and/or hardware), and methods, for identifying, classifying, and/or characterizing biological materials by measuring the molecular weights of protein constituents in such materials and using the molecular information to deduce the organismic source of the biological materials. In preferred embodiments of the invention, biological materials comprising proteins can be subjected to mass spectrometry, or other suitable means for determining mass, in order to determine the molecular weights of the protein constituents. The resulting molecular weight information of the protein constituents can then be used to query databases which contain, among other information, lists of protein molecular weight information and the identity of the organism source from which the information was derived. By comparing the set of protein molecular masses of an unknown, as determined, for instance, in a mass spectrum, against a database containing the molecular masses of proteins present in known organisms, the unknown can be rapidly and reliably identified, classified, or characterized.

The present invention presents a method for rapid identification, classification, and/or characterization of biological materials, such as microorganisms, organisms, organs, tissues, cells, subcellular materials, and the like, which exploits the wealth of information contained in genome and protein sequence databases. The massive efforts to sequence the human genome has brought about a rapid increase in the speed with which DNA sequences from all species are being accumulated in publicly available computer databases. As a result, the complete genomes of many different organisms are now completely known (e.g., National Center for Biotechnology Information (NIH), http://www.ncbi.nlm.nih-.gov/Entrez/Genome/org.html; The C. elegans Sequencing Consortium, Science 1998, 282, 2012–2018; TIGR Microbial Database, http://www.tigr.org/tdb/mdb/mdb.html). See, also, Table 6. There exists complementarity between the genome of an organism, and its respective proteome, i.e. the dynamic entity set of all expressed proteins. In databases, such complementarity is realized via assignment of an amino acid sequence to each "open reading frame" (ORF) in a DNA sequence. By using bioinformatics tools, the complete proteomes of organisms with established DNA sequences have been made available and accessible, e.g., through the Internet. Characterization of such organisms can be achieved through knowledge of their complete genomes or complementary proteomes.

In accordance with the present invention, any instrument, method, process, etc. can be utilized to determine the molecular weight of proteins in a sample. A preferred method of obtaining molecular weight is by mass spectrometry, where protein molecules in a sample are ionized and then the resultant mass and charge of the protein ions are detected and determined.

Any suitable instrument, method, process, etc. for carrying out mass spectroscopy can be utilized. To use mass spectrometry to analyze proteins, it is preferred that the protein be converted to a gas-ion phase. Various methods of protein ionization are useful, including, e.g., fast ion bombardment (FAB), plasma desorption, laser desorption, thermal desorption, preferably, electrospray ionization (ESI) and matrix-assisted laser desorption/ionization (MALDI). Many different mass analyzers are available for peptide and protein analysis, including, but not limited to, Time-of-Flight (TOF), ion trap (ITMS), Fourier transform ion cyclotron (FTMS), quadrupole ion trap, and sector (electric and/or magnetic) spectrometers. See, e.g., U.S. Pat. No. 5,572,025 for an ion-trap MS.

Mass analyzers can be used alone, or in combination to form tandem mass spectrometers. In the latter case, a first mass analyzer can be use to separate the protein ions (precursor ion) from each other and determine the molecular weights of the various protein constituents in the sample. A second mass analyzer can be used to analyze the separated constituents, e.g., by fragmenting the precursor ions into product ions. Any desired combination of mass analyzers can be used, including, e.g., triple quadrupoles, tandem time-of-flights, ion traps, and/or combinations thereof.

Different kinds of detectors can be used to detect the protein ions. For example, destructive detectors can be utilized, such as ion electron multipliers or cryogenic detectors (e.g., U.S. Pat. No. 5,640,010). Additionally, non-destructive detectors can be used, such as an ion trap which is utilized in an ion current pick-up devices which are utilized in quadrupole ion trap mass analyzers or FTMS.

Any source of proteins can be used in accordance with the present invention, including whole organisms, such as multicellular and unicellular organisms, organs, tissues, cells, subcellular structures, and mixtures thereof. Various microorganisms can be utilized, e.g., archeabacteria, bacteria, chlamydiae, *rickettsia*, viruses, *mycoplasma*, molds, yeasts, protozoa, algae, prions, etc. Cells, microorganisms, etc. can be genetically-engineered, altered, modified, etc. Proteins can be extracted from intact or treated materials. Any substrate comprising a biological material can be used. For instance, it may be desirable to characterize organisms found on surfaces, in food, in biological fluids, such as saliva, urine, fecal matter, blood, lymph, or plasma, on materials used to wipe surfaces suspected of containing organisms, in hair, objects handled or contacted by organisms, etc.

Any method of preparing samples for analysis can be used. For MALDI-TOF, a number of sample preparation methods can be utilized including, dried droplet (Karas and Hillenkamp, Anal. Chem., 60:2299–2301, 1988), vacuum-drying (Winberger et al., In *Proceedings of the 41st ASMS Conference on Mass Spectrometry and Allied Topics*, San Francisco, May 31–Jun. 4, 1993, pp. 775a–b), crush crystals (Xiang et al., Rapid Comm. Mass Spectrom., 8:199–204, 1994), slow crystal growing (Xiang et al., Org. Mass Spectrom, 28:1424–1429, 1993); active film (Mock et al., *Rapid Comm. Mass Spectrom.*, 6:233–238, 1992; Bai et al., Anal. Chem., 66:3423–3430, 1994), pneumatic spray (Kochling et al., *Proceedings of the 43rd ASMS Conference on Mass Spectrometry and Allied Topics*; Atlanta, Ga., May 21–26, 1995, p1225); electrospray (Hensel et al., *Proceedings of the 43rd ASMS Conference on Mass Spectrometry and Allied Topics*; Atlanta, Ga., May 21–26, 1995, p947); fast solvent evaporation (Vorm et al., Anal. Chem., 66:3281–3287, 1994); sandwich (Li et al., *J. Am. Chem. Soc.*, 118:11662–11663, 1996); and two-layer methods (Dai et al., Anal. Chem., 71:1087–1091, 1999). See also, e.g., Liang et al., Rapid Commun. Mass Spectrom., 10:1219–1226, 1996; van Adrichem et al., Anal. Chem., 70:923–930, 1998. For example, samples of microorganisms can be lyophilized, extracted into a solution, such as a 70:30 solution of $CH_3CN$:0.1% trifluoroacetic acid, and then embedded in the matrix. Various matrices can be used, e.g., sinapinic acid, 2,5-dihydroxybenzoic acid, alpha-cyano-4-hydroxycinaminnic acid. A sample can be processed in various ways prior to addition to the matrix. For instance, the sample can be extracted, subjected to corona discharge, chromatography, such as HPLC, etc., e.g., to remove particular unwanted constituents (such as lipids, small molecules, high molecular weight constituents) before mass spectrometry.

MALDI-TOF can detect proteins at the attamole level over a wide range of molecular weights. Masses can be determined, e.g., as low as 1000, and as high as a hundred-thousand daltons. Any range of molecular weights can be used in accordance with the present invention, e.g., about 4000–20,000. Masses accurate to about 50 ppm or better will be most reliable in the general case.

In some cases, it may be desirable to obtain more information on a particular protein identified in a mass spectrum. One instance is where a specific peak matches more than one different protein in the searched databases. This can happen when different proteins share the same, or similar, molecular weights. A search of a database in such a case might reveal more than one protein which corresponds to the measured molecular weight of a protein in the sample. To determine which protein in the database corresponds to the peak at issue, the peak protein can be separated from the mixture and subjected to further physical characterization. Separation can be accomplished by any suitable method, e.g., conventional techniques involving, e.g., by cell lysis, extraction, and two-dimensional gel chromatography, capillary electrophoresis, or high performance liquid chromatography.

Useful information includes, amino acid composition, amino acid sequence, proteolytic and enzymatic cleavage patterns, isoelectric point, hydrophobicity, and other physical characteristics. Another scenario where additional information on a protein in spectrum may be warranted is where such protein has not matched any of the proteins listed in the database. Thus, such information can be useful to increase the specificity of the approach.

As mentioned, characterization of individual proteins in mixture can be accomplished using any suitable means. The expanding requirements in proteomics, e.g. for rapid identification of proteins present in a mixture in picomolar amounts, have resulted in the development of powerful MS-based procedures for identity assignment of individual proteins. [9–14] These methods include, but are not limited to, chemical/enzymatic digestion of material (obtained from a single spot in a two-dimensional gel electropherogram, or by other suitable chromatographic technique) and mass spectral determination of the molecular masses of the protein and resulting peptides (peptide mapping). Making use of already available information in protein sequence databases, a comparison can made between proteolytic peptide mass patterns generated "in silico," and experimentally-observed peptide masses. A "hit-list" can be compiled, ranking candidate proteins in the database, based on (among other criteria) number of matches between the proteolytic fragments. Several Web sites are accessible that provide software for protein identification on-line, based on peptide mapping and sequence database search strategies.

Methods of peptide mapping and sequencing using MS are described in WO95/25281, U.S. Pat. No. 5,538,897, U.S. Pat. No. 5,869,240, U.S. Pat. No. 5,572,025, U.S. Pat. No. 5,696,376. See, also, Yates, J. Mass Spec., 33:1–19.1998. The present invention can also be combined with methods that detect small molecules (other than proteins) in samples, such as the method described in WO98/09314. The latter method only measure molecules in the range of about 500–1500 Da, and not more than 1876 Da.

Data collected from a mass spectrometer typically comprises the intensity and mass to charge ratio for each detected event. Spectral data can be recorded in any suitable form, including, e.g., in graphical, numerical, or electronic formats, either in digital or analog form. Spectra is preferably recorded in a storage medium, including, e.g., magnetic, such as floppy disk, tape, or hard disk; optical, such as CD-ROM or laser-disc; or, ROM-CHIPS.

The mass spectrum of a given sample typically provides information on protein intensity, mass to charge ratio, and molecular weight. In preferred embodiments of the invention, the molecular weights of proteins in the sample are used as a matching criterion to query a database. The molecular weights are calculated conventionally, e.g., by subtracting the mass of the ionizing proton for singly-charged protonated molecular ions, by multiplying the measured mass-over-charge-ratio by the number of charges for mutliuply-charged ions and subtracting the number of ionizing protons.

Various databases are useful in accordance with the present invention. Useful databases include, databases which contain genomic sequences, expressed gene sequences, and/or expressed protein sequences. Preferred databases contain nucleotide sequence-derived molecular masses of proteins present in a known organism, organ, tissue, or cell-type. There are a number of algorithms to identify open reading frames (ORF) and convert nucleotide sequences into protein sequence and molecular weight information. Several publicly accessible databases are available, including, SwissPROT/TrEMBL database which contains substantial entries for a variety of organisms, including, *B. subtilis* and *E. coli*. For other databases, see also, e.g., TIGR Microbial Database, http://www.tigr.org/tdb/mdb/mdb.html; VanBogelen et al., *Escherichia coli and Salmonella: Cellular and Molecular Biology*, ASM Press, Washington, D.C., 1996; http://pcsf.brcf.med.umich.edu/eco2 dbase; http://expasy.hcuge.ch/cgi-bin/map2/def?ECOLI.EC02 DBASE. Information contained in the databases includes, e.g., gene name, protein name, E.C. number, category of function, Swiss-Prot accession code, sequence code for Genbank, Kohara phage location, genetic map location, direction of transcription on the chromosome, predicted molecular weight and isoelectric point from DNA sequence, etc.

One or more databases can be searched using any suitable search algorithm. For example, the SwissProt/TrEMBL database ("Expasy," Swiss Bioinformatics Institute) using the Sequence Retrieval System (SRSWWW) module. In general, any search strategy can be utilized in accordance with the present invention.

Typically, a mass spectrometer is equipped with commercial software that identifies peaks above a certain threshold level, calculates mass, charge, and intensity of detected ions. Correlating molecular weight with a given output peak can be accomplished directly from the spectral data, i.e., where the charge on an ion is one and the molecular weight is therefore equal to the numerator value minus the mass of the ionizing proton. However, protein ions can be complexed with various counter-ions and adducts, such as $Na^-$, and $K^+$. In such a case, it would be expected that a given protein ion would exhibit multiple peaks, such as a triplet, representing different ionic states (or species) of the same protein. Thus, it may be necessary to analyze and process spectral data to determine families of peaks arising from the same protein. This analysis can be carried out conventionally, e.g., as described by Mann et al., anal. Chem., 61:1702–1708, 1989.

In matching a molecular mass calculated from a mass spectrometer to a molecular mass predicted from a database, such as a genomic or expressed gene database, post-translation processing may have to be considered. There are various processing events which modify protein structure in a cell, including, proteolytic processing, removal of N-terminal methionine, acetylation, methylation, glycosylation, etc.

A database can be queried for a range of proteins which match the molecular mass of the unknown. The range window can be determined by the accuracy of the instrument, the method by which the sample was prepared, etc. Based on the number of hits (where a hit is match) in the spectrum, the unknown is identified or classified.

A preferred method of the present invention concerns identifying one or more unknown microorganisms in a sample, comprising: searching a sequence database for a plurality of different proteins that have the molecular weights of proteins in a mass spectrum of a sample, wherein said sample comprises a plurality of proteins from one or more unknown microorganisms, whereby said one or more unknown microorganisms are identified.

Identifying is meant in the general sense. For example, when an unknown microorganism is utilized in the aforementioned method, an objective is to determine the character of the unknown. This can mean finding out the particular taxonomic group(s) to which the microorganism belongs, such as its kingdom, phylum, class, order, family, genus, species, variety, and/or strain. By determining that the sample is derived from a bacteria, the sample is thus classified as a bacteria. Identification in this sense can be as precise as the materials and methods allow. For some purposes, it may be enough to identify a sample as derived from a set of possible groups; however, other purposes may demand more precision. For instance, it may be enough for certain purposes to describe the sample as comprising a bacteria, as opposed to a protozoa, or a pathogenic bacteria as opposed to a nonpathogenic bacteria.

In accordance with the method, a database is searched for proteins which have the molecular weights of protein constituents in the sample. A database is a collection of organized information in a form which can be searched and retrieved by a computer, or other electronic processing means. As described above, the searching can be accomplished usually any suitable, effective, search algorithm that can determine the presence of entries in the database which have the same, or within a specified range, molecular weight of proteins in the mass spectrum of the unknown sample. The database, as mentioned earlier, can comprise genomic sequences, expressed genes, protein sequences, protein molecular weights, etc. If the database contains nucleotide information, then this information can be translated into protein data before the searching step, e.g., by identifying an ORF, proteolytic and cleavage sites, glycosylation sites, methylation sites, and other processing which can influence the mass of a protein. In the case where a DNA database is being used to generate and deduce protein information, the knowledge of the protein's characteristics is indirect. Thus, the searching step can be characterized as searching for proteins which are "predicted" to have molecular weights. A search in accordance with the present invention means, e.g., that a database is queried or probed for the presence of a data which matches or corresponds to the measured data, such as the measured data obtained from a mass spectrum.

According to preferred embodiments of the present invention, the database is search for a plurality of different proteins, i.e., more than one, preferably more than 5, etc. In general, identification reliability will depend on a number of factors, including the number of peaks in a matched spectrum matched to proteins in a database, the number and accuracy of proteins predicted from the genome sequence in the mass range under study, etc. By the term "different," it is meant that the proteins arise from different genes, such as a gene coding for a protease and a gene coding for an amylase.

A search strategy can use the information generated by MS, or any other method, to search a database. A simple search and find strategy can be used where the database is queried for proteins which match the molecular weight of the inputted data.

Figure 6:
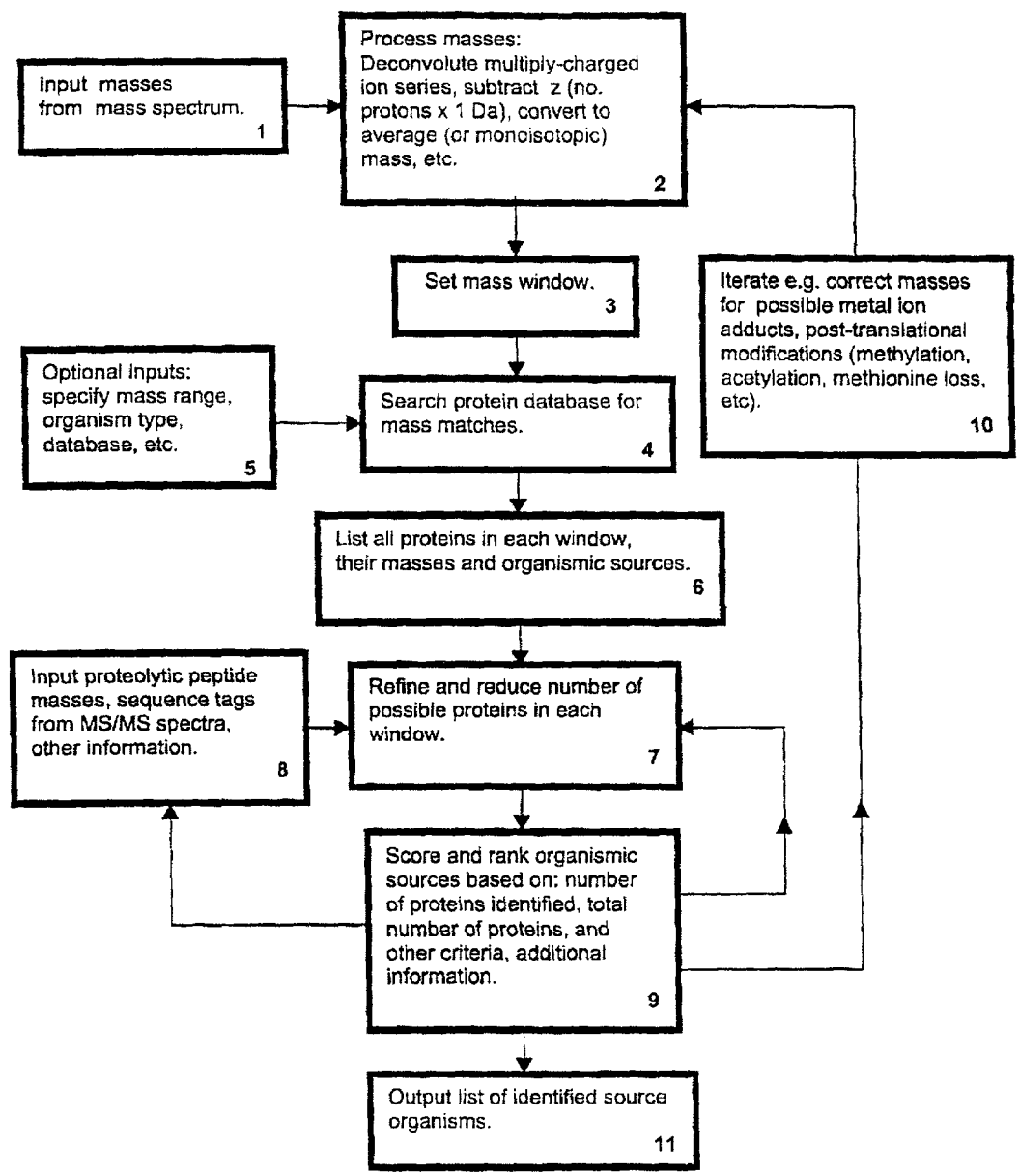
FIG. 6: An example of a flow chart for microroganism and cell identification by mass spectrometry and database searching.

FIG. 6 is an example of a process of identifying an unknown organism, cell, or other biological material. One or more of the steps depicted in the flow chart can be used to identify an organism in accordance with the present invention. In this example, a mass spectrum of a sample comprising proteins from an unknown organism has already been generated using MALDI/TOF spectrometry. The output from the mass spectrometer is represented as a series of m/z values, where m is the mass of a protein plus the mass of a proton or other charging species, and z is the net number of charges carried by the ion and is used as the initial input 1. The input masses are processed 2, e.g., by subtracting one dalton to correct for the proton added to the protein when it is ionized through gas-phase proton transfer reaction of MALDI. The input data can additionally processed by determined an average molecular weight or a monoisotopic mass. A protein will typically be represented in a mass spectrum by more than one peak because of the presence in it of more than one isotope. Carbon, for instance, occurs in nature as C-12 or C-13 in a ratio of about 100:1. Therefore, if a compound contains a single carbon, it would be expected that 99% of it would be C-12 and 1% of it would be C-13. The mass spectrum of such compound would therefore have at least two peaks, each corresponding to a different carbon isotope. As the number of carbon atoms in a molecule increases, there is an increasing number of polyisotopic molecules, comprising varying ratios of the different carbon isotopes. A mass spectrum of such a compound would contain multiple peaks for each polyisotopic molecule. A compound containing a plurality of atoms represented by more than one isotope will have a complex pattern of spectral peaks. Such complex spectral information can be processed in a number of ways. A average mass can be calculated, e.g., using the empirical spectral information. Alternatively, a monisotopic mass can be calculated where a mass is derived where the mass of only one isotope of each atom is represented in the molecule.

Before database searching is initiated, a mass window is set 3 to define a mass range in which matches in the database will be scored as hits. The mass window for a particular query can be set based on various criteria. One consideration is the accuracy of the instrument. For instance, if the instrument can only measure values within three daltons, then the mass window could be for ±3 Da. Other considerations, include, post-translational processing. The accuracy of the instrument can be determined routinely, e.g., using known standards and calibrating the instrument using an external and internal standard.

The processed data resulting from 2 is used as input data to initiate a search 4 of a database containing protein masses. In preferred embodiments, the database comprises nucleotide sequence information which has been analyzed to predict the occurrence of open reading frames (ORF) and the calculated molecular masses of such ORFs. As mentioned above, various public and private databases are available that contain calculated protein mass information, or which can be mined by available software to derive such information. The search mode queries the database for proteins having molecular masses which match up with the molecular masses in the mass spectrum input data 2. For each peak in the input data 2, the database is queried and a list is generated of putative database proteins which match it. A match is identified in the database if it possesses the same mass as the peak, or if it is within the range indicated in the mass window 3.

A first list 6 can be generated which reflects the masses and organismic sources for each match. For example, each mass spectral peak of 2 can be associated with a family of proteins, representing proteins of the same molecular mass but from different organisms and proteins within the mass range set in 3.

The data in 6 can optionally be refined 7 by inputting additional data 8, e.g., from fragmented precursor ions of 1 and collecting data of peptide mass, sequence tag information from mass spectra, or other types of downstream information on the constituent proteins. Such data, or orthogonal information, can, e.g., increase certainty that the identification is correct and/or reduce the number of positive hits identified in a search. When a search identifies X possible proteins in the database which match the query by being within the mass window set in 3, a step 8 can be used to reduce the number of possible hits. When the queried database contains amino acid sequence information (deduced or experimentally-derived), sequence information or proteolytic information can be used to determine which specific hit, in the set of hits identified for the specified mass range, corresponds to the data point of interest in the mass spectrum. For example, amino sequence or composition information obtained from a peak of interest can be used to search the set of hits identified as matching the peak of interest to ascertain which hit contains the sequence information. Sequence can information can be highly specific, eliminating all other peaks having the same molecular weight from the list generated in 7. Amino acid composition information can also be used a refining tool, although it may be less specific. Any supplemental information on the physical characteristics of a protein can be used to confirm and/or reduce the number of hits identified in a search, including, sequence information as mentioned, cleavage patterns (chemical or enzymatic), isoelectric point, hydrophobicity as deduced from chromatography, immuogenicity, etc.

The data from 6 or 7 can then be scored to generate an output list 10 which lists the possible organisms sources of the mass spectrum. The identified organismic sources can be ranked based on a number of criteria, including, but not limited to, total number of proteins identified as matching an organismic source, orthogonal information obtained in 8, etc. Table 1, for instance shows that *B. subtilis* contains 12/15 or 80% matching peaks and *E. coli* contains 6/15 or 40% matching peaks, If percent match is the sole criteria, *B. subtilis* would be ranked above *E. coli*.

Optionally, the proteins which are unidentified (e.g., the three proteins listed in Table 1 for *B. subtilis*) in the list can be subjected to further analysis in an interation step 10. One reason that a matching protein is not identified in the database may be that the protein is subjected to post-translational modifications and therefore does not have the molecular weight predicted by ORF analysis.

An advantage of the present invention is that it can be independent of the specific ionization technique and mass analyzer utilized, alleviating the requirement for rigorous reproducibility, crucial in currently used fingerprint-based approaches. The approach introduced here is independent of relative signal intensities in the mass spectrum. It does not even require that the same set of proteins be expressed and/or detected in each analysis of the same organism, only that a set is characteristic so that it can be associated with a microorganism source. The particular choices of sample preparation, ionization and mass analysis for obtaining mass spectra are not restrictive for the described approach, which also has a potential to be used for identification of cells from individual tissues.

The present invention can be used in variety of different ways and settings and has useful applications in the lab, field, and environmental testing. For example, it can be used in human and veterinary medicine to diagnose normal and pathological conditions from biological materials, such as blood, plasma, urine, sperm, fecal matter, and saliva. The present invention is also useful in research and industry. Food samples can be obtained from food materials suspected of contamination.

EXAMPLES

For the purpose of illustrating the feasibility of the method MALDI TOF mass spectrometry was employed. The described database search method is not restricted to that specific instrument combination and sample preparation. Sinapinic acid (SA) or ∝-cyano-4-hydroxycinnamic acid (CHCA) 50 mM in 70:30 $CH_3CN:H_2O$, and an equimolar mixture of SA and 4-methoxycinnamic acid (MCA) in 70:30 $CH_3CN:H_2O$ were used as matrixes. The microorganisms studied were: *B. subtilis* (strain 168, ATCC# 23857) and *E. coli* (ATCC#11775). They were grown in-house according to standard procedures; 8 g/l nutrient broth (Difco Labs, Detroit, Mich.) was used as a growth medium, after harvesting the material was centrifuged for 10 min at $10^4$ g and washed with water three times prior to lyophilization for prolonged storage at $-10°$ C. Lyophilized vegetative cells were suspended in a 70:30 solution of $CH_3CN$: 0.1% trifluoroacetic acid at a concentration of 5 mg/ml. *B. subtilis* suspension (0.2 µl) was deposited on the sample slide before MALDI mass spectrometry. For *E. coli* and *B. subtilis* was prepared by mixing suspensions of the two microorganisms on the slide prior to CPD treatment and MALDI mass spectrometry. In some experiments, an internal mass calibration standard (a solution of bovine insulin and bovine ubiquitin) was added to the *E. coli* sample/matrix mixture on the sample slide in order to increase the accuracy of mass determination. For *B. subtilis*, external calibration of the instrument using a mixture of proteins (bovineinsulin, bovine ubiquitin and horse heart cytochrome C) was performed prior o running the samples. All proteins were obtained from Sigma Chemical Co. (St. Louis, Mo.).

Positive ion mass spectra (typically from 50 single laser shots rastered uniformily across the sample spot) were recorded in linear mode at 20 kV accelerating voltage and a delay of 0.34 µs. The estimated $N_2$ laser fluence was around 10 mJ·cm$^{-2}$.

A search by protein molecular mass ($M_r$) and based on the set of protein molecular weights in the spectra was carried out in the SwissProt/TrEMBL database ("Expasy", Swiss Bioinformatics Institute) using the Sequence Retrieval System (SRSWWW) module at http://expasy.hcuge.ch/srs5/. A interactive window ("Alternative Query Form") allows search by a number of classifiers. In case we chose average protein MW as the primary classifier. We selected a±3 Da MW window, and the only restriction applied in the query was the choice of the "bacteria" protein subset of the database (in earlier release of SwissPROT the identifier "prokaryota" was also available). Thus protein identifies and organismic sources were tentatively assigned for all peaks from the experimental spectra within the range from 4 to 15 kDa.

Under the conditions used, the MALDI spectra (FIG. 2) of *B. subtilis* and *E. coli* contain multiple peaks between 4 and 10 kDa with a signal to noise ratio better than 3. They are listed in Tables 1 and Tables 2, respectively. A database search was performed, based on the observed masses. It was assumed that singly-protonated molecules were detected i.e., a proton mass was subtracted from the observed mass in order to obtain the average $M_r$. In assigning the respective peaks (i.e. Proteins with $M_r$ within the $M_r$ window chosen: ±3 Da), the organisms from which each potential protein originates, are also determined. These are presented in Tables 1 and 2. From, Table 1, One microorganism, *B. subtilis*, is identified as the source of 12 of the 15 peaks. There are two "runner-ups" in that example, that provide matches for 6 and 5 of the 15 major peaks. It is evident from Table 2 that 13 *E. coli* proteins match observed peaks (out of 17 total), while one microorganism matches 5 of the 17 peaks. The possibility that unmatched peaks can correspond to alkali cation adducts and/or post-translationally modified products (including proteolytic fragments) of proteins already present in the database will be explored in a software implementation of the described approach.

Figure 2A:
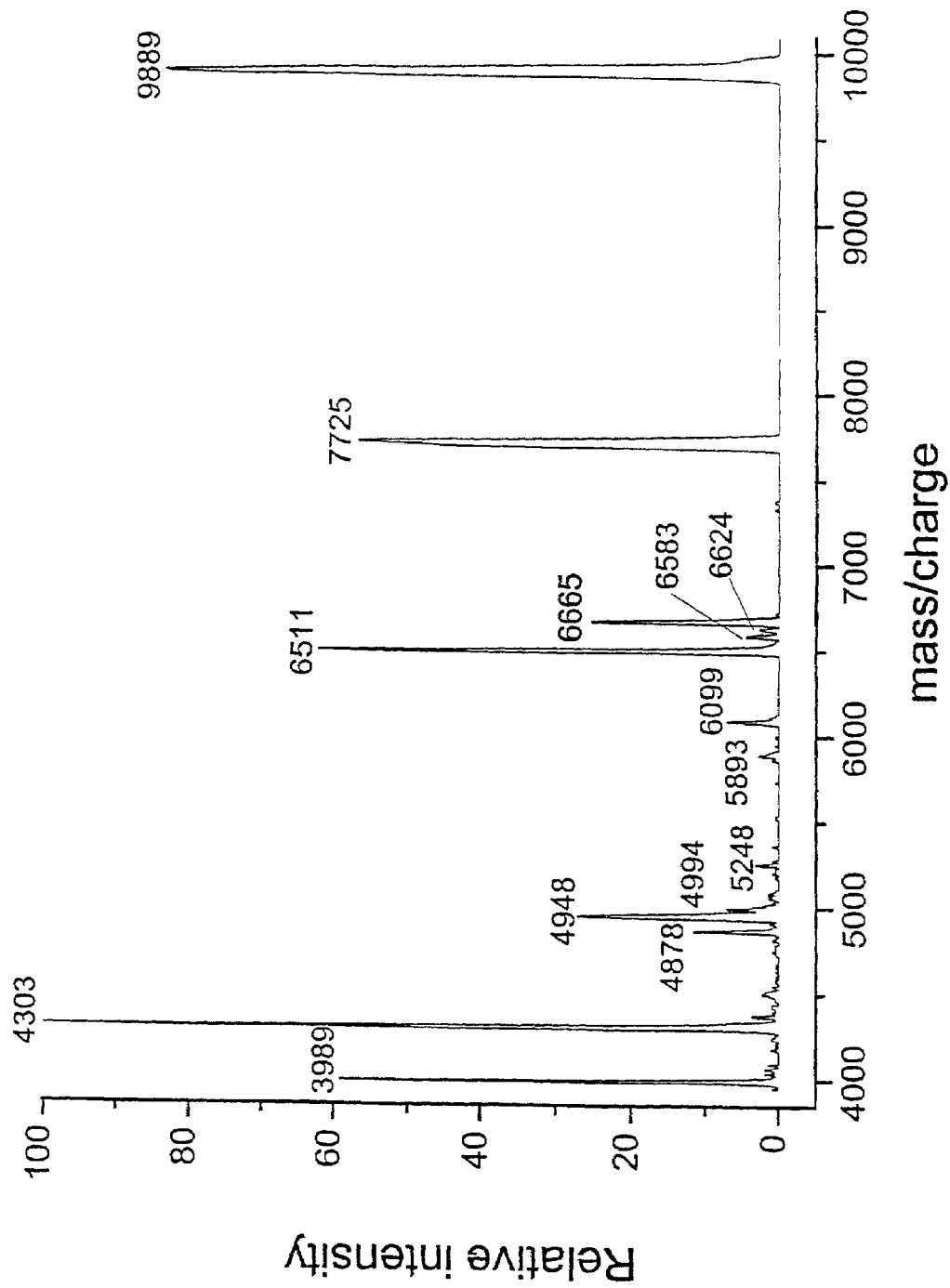
FIG. 2: Positive ion MALDI spectra from: a) B. subtilis (8 hours growth time), matrix—SA; and b) E. coli (32 hours growth time), matrix —CHCA.
Figure 2B:
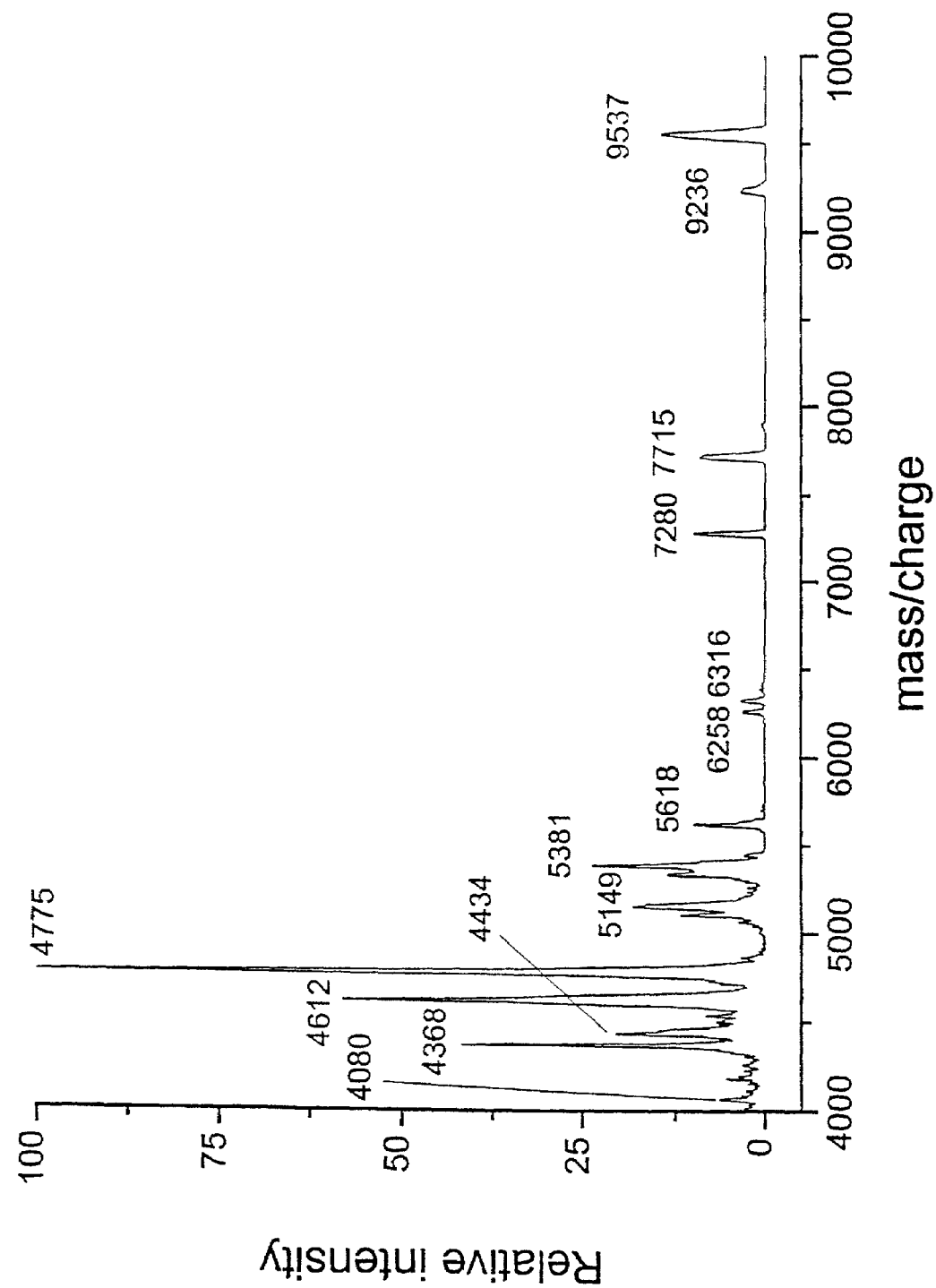

As already pointed out, there exist inherent problems with the reproducibility of MADLI mass spectra of the same organism—*E. coli* [26,29,30] shows that they do not match each other of the spectrum in FIG. 2*b*. However, searching the proteome database for masses observed in each spectrum leads to the positive identification of the bacteria in each case (Tables 3–5). This is not surprising since all spectra should reflect the presence of expressed proteins from the same genome. the same type of robustness can be illustrated by comparing the MALDI spectra from the same sample of *E. coli*, obtained in different matrixes. The spectra have different fingerprints—peaks above 5 kDa are more prominent in the spectra obtained with MCA:SA matrix (FIG. 3.*a*), in comparison to spectra with CHCA matrix (FIG. 2*b*). However, the database search method results in positive identification of the species in each spectrum (Tables 2 and 7). Effects of incubation time on experimentally obtained mass spectra from *E. coli* have been discussed in the literature [31]. Spectra from *E. coli* harvested after 8 and 32 hours of growth are compared on FIG. 3.*b* and 2*b*. Again the overall spectral appearance is different for the two samples. Nevertheless the identification is straightforward in both cases (Tables 2 and 7). It appears that experimental factors such as choice of an "appropriate" MADLI matrix, variability in the levels of protein expression, etc. will have limited influence when microorganisms are identified by searching the proteome database.

REFERENCES

1. National Center for Biotechnology Information (NIH), http://www.ncbi.nlm.nih.gov/Entrez/Gerome/org.html
2. The *C. elegans* Sequencing Consortium, *Science* 1998, 282, 2012–2018
3. Arigioni, F.; Talabot, F.; Peitsch, M.; Edgerton, M.; Meldrum, E.; Allet, E.; Fish, R.; Jamotte, Th.; Curchod, M.-L.; Loferer, H. Nat. Biotechnology 1998, 16,851–856.

4. *Bioinformatics: A Practical Guide to the Analysis of Genes and Proteins*; Baxevanis, A.; Oulette, B., Ed.; Methods of Bichemical Analysis 39; Wiley interscience: New York, 1998.
5. Roepstorff, P. *Curr. Opin. in Biotechnol.* 1998, 8, 6–13
6. I. Humphrey-Smith, W. Blackstock, *J. Protein Chem.* 1997, 231, 1–6.
7. James, P. *Biochem. Biophys. Res. Commun.* 1997, 231 1–6
8. Kuster, B.; Mann, M. *Curr. Opinions in Struct. Biology* 1998, 8, 393–400
9. Henzel, W.; Billeci, T.; Stults, J.; Wong, S.; Grimley, C.; Watanabe, C. *Proc. Natl. Acad. Sci. USA*, 1993, 90,5011–5015
10. Mann, M.; Hojrup, P.; Roepstorff, P. *Biol. Mass Spectrum.* 1993, 22, 338–345.
11. Pappen, D.; Hojrup, P. Bleasby, A. *Current Biology* 1993, 3, 327–332.
12. James, P.; Quandroni, M.; Carafoli, E.; Gonnet, G. *Biochem. Biophys. Res. Commun.* 1993, 195,58–64.
13. Yates III, J. R.; McCormack, A.; Eng, J. *Anal. Chem.* 1996, 68, 534A–540A.
14. Fenyö, D.; Qin, J.; Chait, B. *Electrophoresis* 1998, 19, 998–1005.
15. prospector.uscf.edu.
    www.proteometrics.com
    www.mann.enmbl-heidelberg.de/Services/PeptideSearch
    cbrg.inf.ethz.ch/MassSearch.html
    expasy.hcuge.ch
    www.sequet.dlac.uk/mowse.html
16. Jensen, O.; Podtelejnikov, A.; Mann, M. *Rapid Commun. Mass Spectrum.* 1996, 10, 1371–1378.
17. Mortz, E.; O'Connor, P. Roepstorf, P.; Kelleher, N.; Wood, T.; McLafferty, F.; Mann, M. *Proc. Natl. Acad. USA* 1996, 93, 8264–8267.
18. Yates III, J. R.; Eng, J. U.S. Pat. No. 553,897 (issued Jul. 23, 1996). "Use of Mass Spectrometry Fragmentation Patterns of peptides to Identify Amino Acid Sequences in Databases."
19. Anhalt, J. P.; Fenselau, C. *Anal. Chem.* 1975, 47, 219–225.
20. Heller, D.; Fenselau, C.; Cotter, R.; Demirev, P.; Olthoff, J.; Honovich, J.; Uy, M.; Tanaka, T.; Kishimoto, Y. *Biochem. Biophys. Res. Commun.* 1987, 142, 194–199.
21. *Mass Spectrometry for the Chacracterization of Microorganisms*; Fenselau, C., Ed.; ACS Symposium Series 541; Am. Chem. Soc.: Washington D.C., 1994.
22. Cain, T.; Lubman, D.; Weber Jr., W *Rapid Commun. Mass Spectrom.* 1994, 8, 1026–1030.
23. Claydon, M.; Davey, S.; Edwards-Jones, V.; Gordon, D. *Nature Biotechnology* 1996, 14, 1584–1586.
24. Holland, R.; Wilikes, J.; Rafii, F.; Sutherland, J.; Person, C.; Voorhees, K.; Lay, J. *Rapid Commun. Mass Spectrom*
25. Krishnamurthy, T.; Ross, P.; Rajamani, U. *Rapid Commun. Mass Spectrom.* 1996, 10, 883–888
26. Arnold, R.; Reilly, J.; *Commun. Mass Spectrom.* 1998, 12, 630–636.
27. Welham, K.; Domin, M.; Scannell, D.; Cohen, E.; Ashton, D.; *Rapid Commun. Mass Spectrom.* 1998, 12, 176–180
28. Haag, A.; Taylor, S.; Johnston, K.; Cole, R. *J Mass Spectrom.* 1998, 33, 750–756
29. Wang, Z.; Russon, L.; Li, L.; Roser, D.; Long, S. R. *Rapid Commun. Mass Spectrom.* 1998, 12, 456–464.
30. Dai, Y.; Li, L.; Roser, D.; Long, S. R. Rapid Commun. Mass Spectrom. 1999, 13, 73–78.
31. Arnold, R.; Reilly, J. *A Study of Bacterial Culture Growth by MALDI-MS of Whole Cells*; Proceedings of the 46th ASMS Conference on Mass Spectrometry and Allied Topics, Orlando, Fla., May 31–Jun. 4, 1998, p. 180.
32. Birmingham, J.; Demirev, P.; Ho, Y-P.; Thomas, J.; Bryden, W.; Fenselau, C. *Rapid Commun. Mass Spectrom.* 1999, 13, 604–606.
33. Das, S.; Yu, L.; Gaitatzes, C.; Roger, R.; Freeman, J.; Blenkowska, J.; Adams, R. M.; Smith, T. F. *Nature* 1997, 385, 29–30.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

The entire disclosure of all applications, patents, publications, cited above and in the figures are hereby incorporated in their entirety by reference, including Demirev et al., Anal. Chem., 71:2732–2738, 1999.

From the foregoing description, one skilled in the art can easily ascertain the essential characteristics of this invention, and without departing from the spirit and scope thereof, can make various changes and modifications of the invention to adapt it to various usages and conditions.

TABLE 1

Ranking of organisms according to matched peaks in *B. subtilis* spectrum (FIG. 2.a).

| Organism* | Observed mass (Da) | | | | | | | | | | | | | | |
|---|---|---|---|---|---|---|---|---|---|---|---|---|---|---|---|
| | 3988 | 4302 | 4506 | 4877 | 4947 | 4993 | 5247 | 5892 | 6098 | 6510 | 6582 | 6623 | 6664 | 7724 | 9888 |
| B. subtilis | X | X | X | X | | X | X | X | X | X | | X | | X | X |
| E. coli | | X | | X | | | X | X | | X | X | | | | |
| B. burgdorferi | X | X | | X | X | | | X | | | | | | | |
| M. tuberculosis | | | | | | | X | | X | | X | | | X | |
| P. aeruginosa | | X | | | | X | | | | | | | | | |
| M. leprae | | | | | | | | | | | X | | | | X |

*Only organisms with more than one matching peak (within ±3 Da) are listed.

TABLE 2

Ranking of organisms according to matched peaks in *E. coli* spectrum (FIG. 2.b).

| Organism* | \multicolumn{17}{c}{Observed mass (Da)} |
|---|---|---|---|---|---|---|---|---|---|---|---|---|---|---|---|---|---|
| | 4079 | 4367 | 4433 | 4538 | 4611 | 4774 | 5101 | 5149 | 5335 | 5380 | 5617 | 6257 | 6315 | 7279 | 7714 | 9235 | 9536 |
| *E. coli* | X | X | X | X | X | | X | | | X | X | | X | X | X | X | X |
| *H. influenza* | | | | | | | X | | | | | X | X | | X | X | |
| *B. subtilis* | | | | | | | | | | | | X | X | | X | | X |
| *M. leprae* | | | | | | | | | | X | X | | X | | X | | |
| *B. burgdorferi* | X | | | X | | X | | | | | | | | | X | | |
| *S. typhimurium* | X | | | X | | | | X | | | | | | | | X | |
| *H. pyroli* | | | | | | | | | X | | | | | X | | | |
| *Synechococcus* sp. | | X | | | | | | | | | | | | | X | | |
| *M. tuberculosis* | | | | | | | | | | | | | | | X | X | |

*Only organisms with more than one matching peak (within ±3 Da) are listed.

TABLE 3

Ranking of organisms according to matched peaks in *E. coli* spectrum (FIG. 1.b of Ref. 29).

| Organism* | \multicolumn{12}{c}{Observed mass (Da)} |
|---|---|---|---|---|---|---|---|---|---|---|---|---|
| | 4362 | 4711 | 5076 | 5752 | 6255 | 7272 | 7708 | 8447 | 9067 | 9424 | 10464 | 10760 |
| *E. coli* | X | X | X | | X | X | X | X | X | X | X | X |
| *H. influenza* | X | | X | | X | X | X | | | X | X | |
| *B. subtilis* | | | | X | X | X | X | X | | | | X |
| *Synechococcus* sp. | X | | | | | X | X | | | | X | X |
| *H. pyroli* | | X | | X | | X | | | | | | |
| *M. leprae* | | | | | | | | | | X | X | X |
| *Rhizobium* sp. | | | | | | X | | | | X | X | |
| *B. burgdorferi* | | X | | X | | | | | | | | |
| *M. tuberculosis* | | | | | | | X | | | X | | |
| *S. typhimurium* | | | | X | | | | | | | | X |

*Only organisms with more than one matching peak (within ±5 Da) are listed.

TABLE 4

Ranking of organisms according to matched peaks in *E. coli* spectrum (FIG. 1.a of Ref. 30).

| Organism* | \multicolumn{11}{c}{Observed mass (Da)} |
|---|---|---|---|---|---|---|---|---|---|---|---|
| | 3636 | 4365 | 4532 | 4769 | 6547 | 7271 | 7333 | 9061 | 9535 | 9737 | 13093 |
| *E. coli* | | X | X | | | X | X | X | X | X | X |
| *B. subtilis* | | | | X | | X | X | X | X | X | X |
| *Synechococcus* sp. | | X | X | | | X | | | X | X | |
| *B. burgdorferi* | X | | X | | | | X | | X | | |
| *H. influenza* | | X | | | X | | | | X | | |
| *Rhizobium* sp. | | | | | X | X | | | X | | |
| *H. pyroli* | | | | X | X | | | | | | |
| *M. tuberculosis* | | | | | | | | | | X | X |
| *S. typhimuriuim* | X | | X | | | | | | | | |

*Only organisms with more than one matching peak (within ±5 Da) are listed.

TABLE 5

Figure 4:
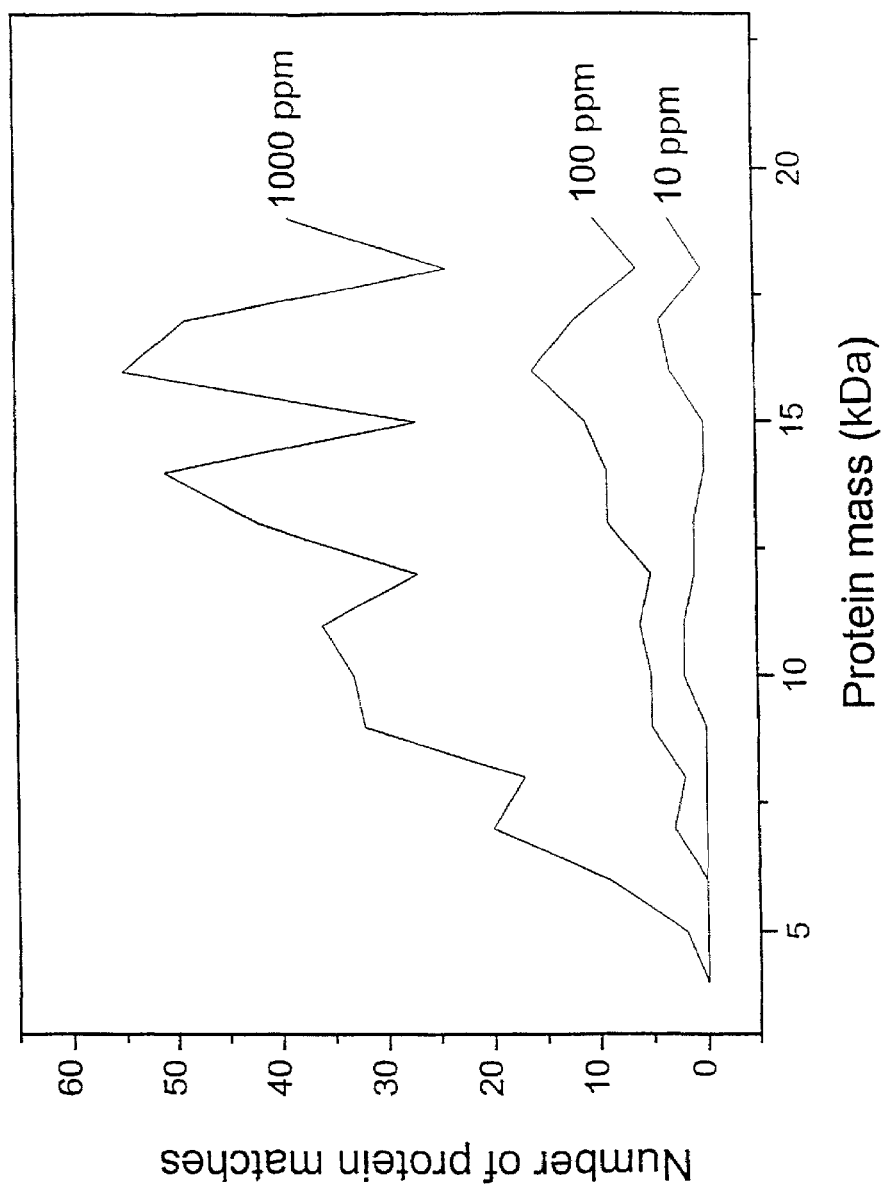
FIG. 4: Number of proteins combined from B. subtilis and E. coli with masses within a predetermined mass window (in ppm) as a function of molecular mass.

Ranking of organisms according to matched peaks in *E. coli spectrum* (FIG. 4 of Ref. 26).

| Organism* | \multicolumn{7}{c}{Observed mass (Da)} |
|---|---|---|---|---|---|---|---|
| | 5100 | 5380 | 7280 | 8320 | 9070 | 9530 | 9740 |
| *E. coli* | X | X | X | X | X | X | X |
| *B. subtilis* | | | | | X | X | X |
| *M. tuberculosis* | | | | | X | X | X |
| *H. pyroli* | | | X | X | | | |
| *B. burgdorferi* | | | | | X | X | |
| *H. influenza* | X | | | | | X | |
| *E. cloacae* | X | | X | | | | |
| *Synechocystis* sp. | | | | | | X | X |

*Only organisms with more than one matching peak (within ±5 Da) are listed.

TABLE 6

Figure 3A:
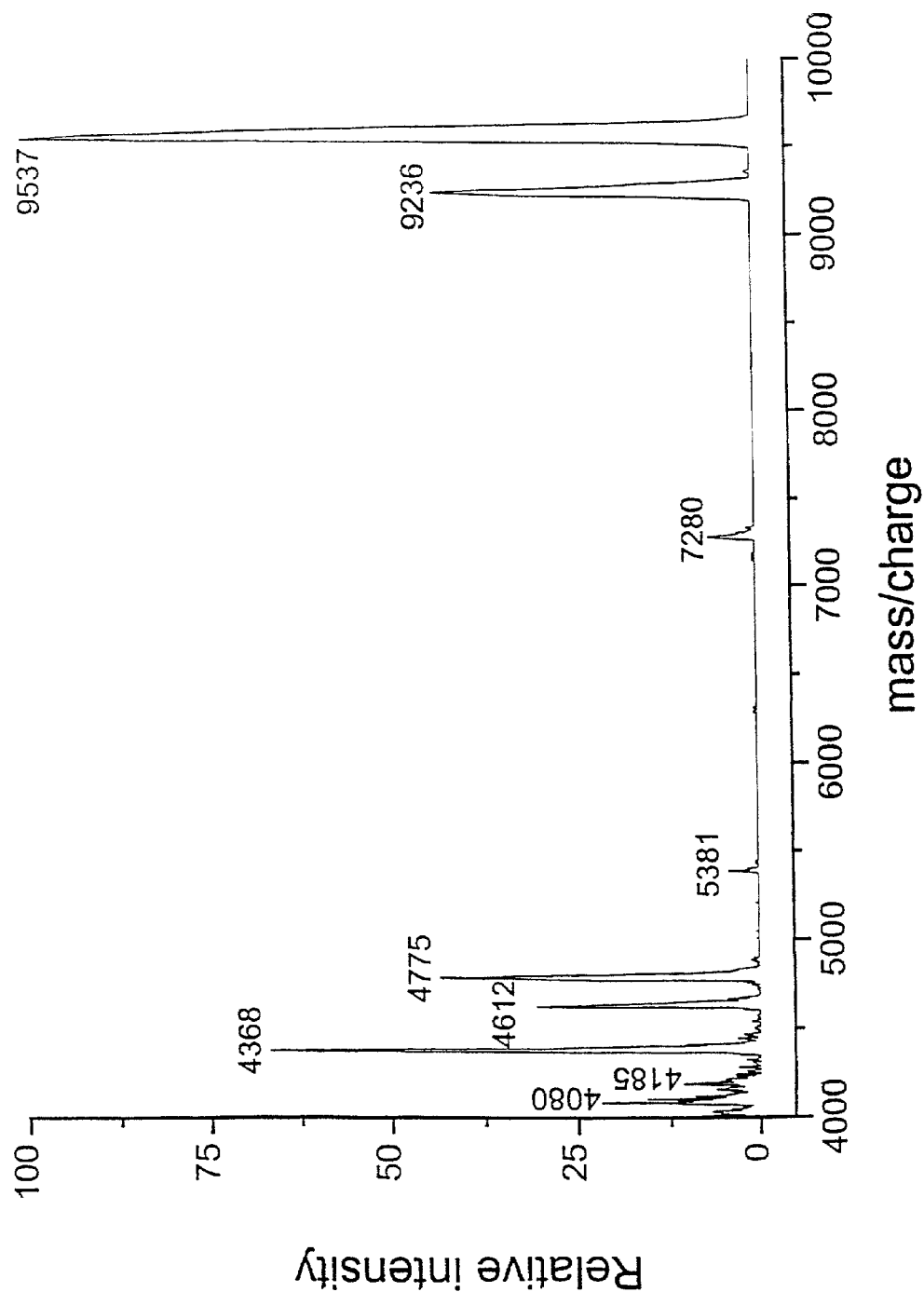
FIG. 3: Positive ion MALDI spectra from: a) E. coli (32 hours growth time), matrix—MCA:SA mixture; and b) E. coli (8 hours growth time), matrix—CHCA.
Figure 3B:
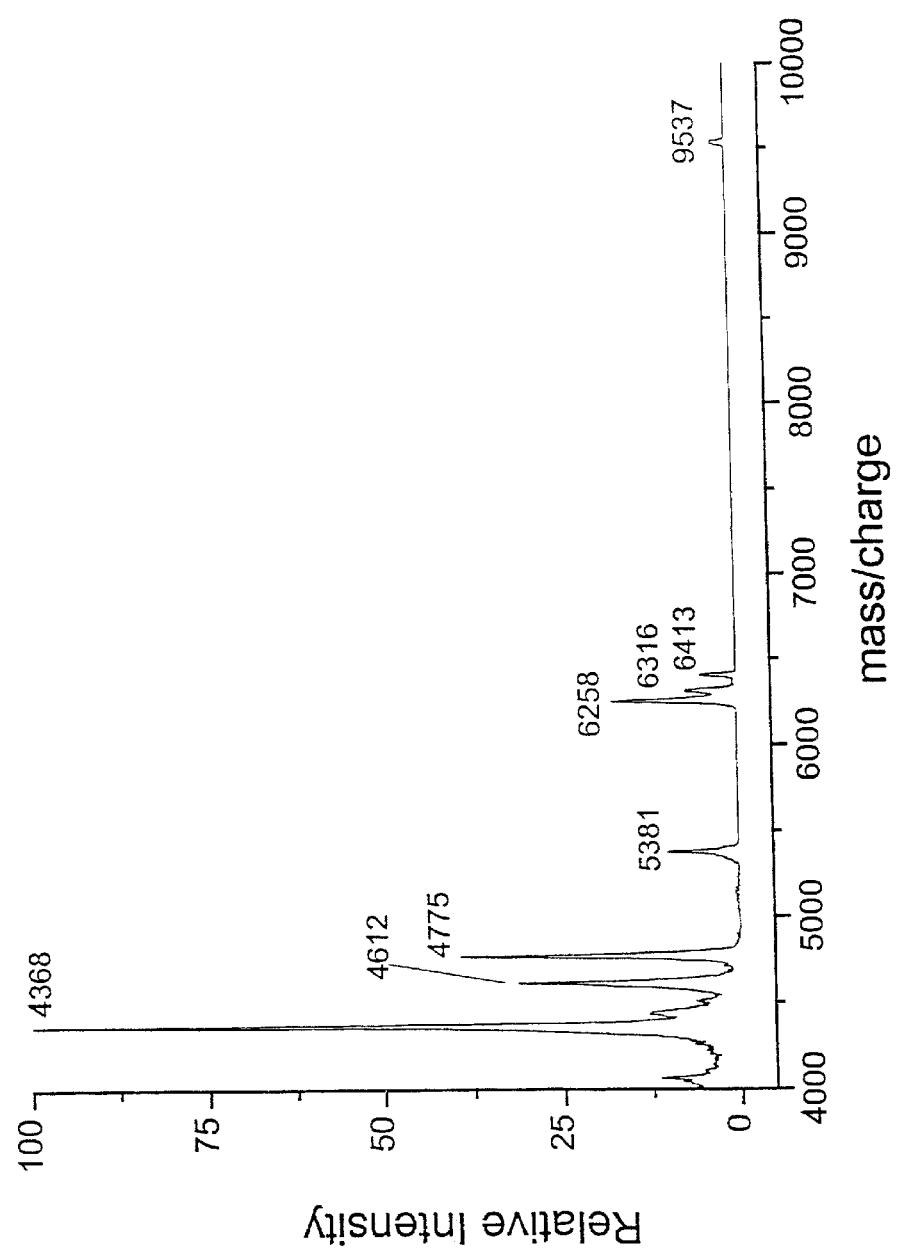

Ranking of organisms according to matched peaks in *E. coli* spectrum (FIG. 3.a).

| Organism* | Observed mass (Da) | | | | | | | | |
|---|---|---|---|---|---|---|---|---|---|
| | 4079 | 4184 | 4367 | 4612 | 4774 | 5380 | 7279 | 9235 | 9537 |
| *E. coli* | X | | X | X | | X | X | X | X |
| *B. burgdorferi* | X | X | | | X | | | | |
| *M. leprae* | | | | | | X | X | X | |
| *Synechococcus* sp. | | X | X | | | | | | |
| *S. typhimurium* | X | | | | | | | X | |

*Only organisms with more than one matching peak (within ±3 Da) are listed.

TABLE 7

Ranking of organisms according to matched peaks in *E. coli* spectrum (FIG. 3.b).

| Organism* | Observed mass (Da) | | | | | | | | |
|---|---|---|---|---|---|---|---|---|---|
| | 4079 | 4367 | 4433 | 4611 | 4774 | 5380 | 6257 | 6315 | 6412 | 9536 |
| *E. coli* | X | X | X | X | | X | | X | X | X |
| *B. subtilis* | | | | | | | X | X | | X |
| *H. influenza* | | | | | | | X | X | | |
| *B. burgdorferi* | X | | | X | | | | | | |
| *M. leprae* | | | | | | X | | | X | |
| *Synechocystis* sp. | | X | | | | | | | X | |

*Only organisms with more than one matching peak (within ±3 Da) are listed.

TABLE 8

Figure 5:
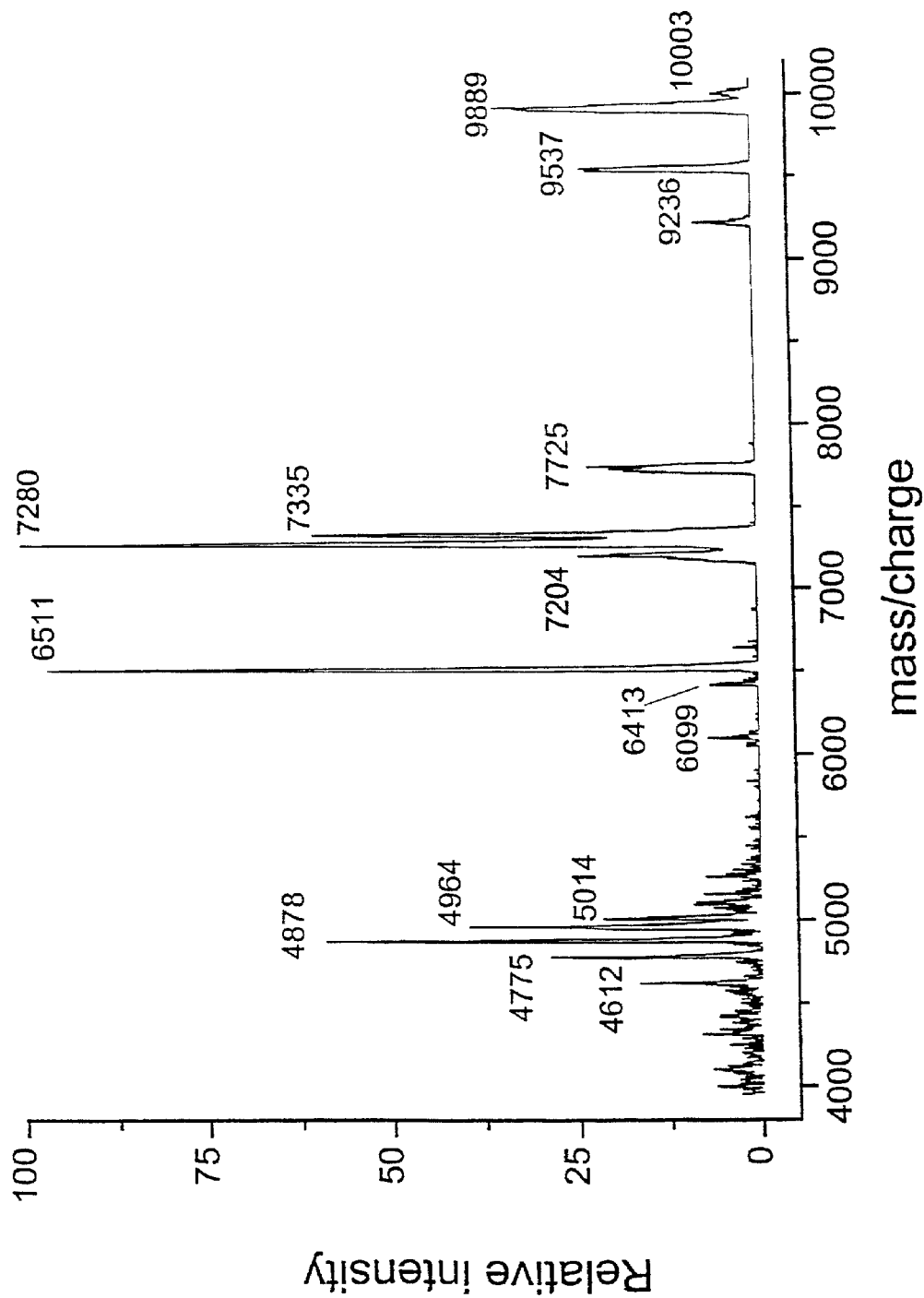
FIG. 5: Positive ion MALDI spectrum from a mixture of B. subtilis and E. coli, matrix —SA.

Ranking of organisms according to matched peaks in spectrum of *B. subtilis* and *E. coli* mixture (FIG. 5).

| Organism* | Observed mass (Da) | | | | | | | | | | | | | | |
|---|---|---|---|---|---|---|---|---|---|---|---|---|---|---|---|
| | 4611 | 4774 | 4877 | 4963 | 5013 | 6098 | 6412 | 6510 | 7203 | 7279 | 7334 | 7724 | 9235 | 9536 | 9888 | 10002 |
| *E. coli* | X | | X | X | | | X | X | X | X | X | | X | X | | X |
| *B. subtilis* | | | X | | X | X | | X | X | | | X | | X | X | X |
| *M. leprae* | | | | | | | X | X | X | | | | X | | X | X |
| *Synechocystis* sp. | | | | | | | X | | X | X | | | | | | X |
| *B. burgdorferi* | | X | X | | X | | | | | | | X | | | | |
| *H. influenza* | | | | X | | | | | | | | | X | | | |
| *M. tuberculosis* | | | | | | X | | | | | | X | | | | |
| *S. typhimurium* | | X | | | | | | | | | | | X | | | |

*Only organisms with more than one matching peak (within ±3 Da) are listed.

TABLE 9

| Genome | Publication |
|---|---|
| *Haemophilus influenzae* Rd | Fleischmann et al., Science 269:496–512 (1995) |
| *Mycoplasma genitalium* | Fraser et al., Science 270:397–403 (1995) |
| *Methanococcus jannaschii* | Bult et al., Science 273:1058–1073 (1996) |
| *Synechocytis* sp. | Kaneko et al., DNA Res. 3:109–136 (1996) |
| *Mycoplasma pneumoniae* | Himmelreich et al., Nuc. Acid Res. 24: 4420–4449 (1996) |
| *Saccharomyces cerevisiae* | Goffeau et al., Nature 387 (Suppl.) 5–105 (1997) |
| *Helicobacter pylori* | Tomb et al., Nature 388:539–547 (1997) |
| *Escherichia coli* | Blattner et al., Science 277:1453–1474 (1997) |
| *Methanobacterium thermoautotrephicum* | Smith et al., J. Bacteriology 179: 7135–7155 (1997) |
| *Bacillus subtilis* | Kunst et al., Nature 390:249–256 (1997) |
| *Archaeoglobus fulgidus* | Klenk et al., Nature 390:364–370 (1997) |
| *Borrelia burgdorferi* | Fraser er al., Nature 390:580–586 (1997) |
| *Aquifex aeolicus* | Deckert et al., Nature 392:353 (1998) |
| *Pyrococcus horikoshii* | Kawarabayasi et al., DNA Research 5: 55–76 (1998) |
| *Mycobacterium tuberculosis* | Cole et al., Nature 393:537 (1998) |
| *Treponema pallidum* | Fraser et al., Science 281:375–388 (1998) |
| *Chlamydia trachomatis* | Stephens et al., Science 282:754–759 (1998) |
| *Plasmodium falciparum* Chr2 (isolate 3D7) | Gardner et al., Science 282:1126–1132 (1998) |
| *Rickettsia prowazekii* | Andersson et al., Nature 396:133–140 (1998) |
| *Helicobacter pylori* | Alm et al., Nature 397:176–180 (1999) |
| *Leishmania major* Chr1 | Myler et al., Proc. Natl. Acad. Sci. USA 96:2902–2906 (1999) |
| *Chlamydia pneumoniae* | Kalman et al., Nat. Genet. 21:385–389 (1999) |
| *Aeroyrum pernix* | Kawarabayasi et al., DNA Research 6: 83–101 (1999) |
| *Thermotoga maritima* | Nelson et al., Nature 399:323–329 (1999) |

The invention claimed is:

1. A method of identifying one or more unknown microorganisms in a sample comprising:
   searching a database for the molecular weights of a plurality of intact, undigested proteins obtained from a mass spectrum of a sample, wherein said one or more unknown microorganisms are identified,
   wherein said sample comprises a plurality of said intact, undigested proteins from one or more unknown microorganisms, and said database is searched for more than one different said protein, and
   wherein said database comprises molecular weight information deduced from nucleotide or protein sequence information obtained from genomic sequencing of known microorganisms, wherein the intact, undigested proteins have been fragmented by exposure to chemical or enzymatic digestion after isolation from microorganism.

2. A method of claim 1, wherein the database comprises protein sequence information.

3. A method of claim 1, wherein the database comprises nucleotide sequence information.

4. A method of claim 1, wherein the mass spectrum is obtained from MALDI-TOF mass spectrometry.

5. A method of claim 1, wherein the mass spectrum data is obtained by electrospray on a time-of-flight, quadrupole, or ion trap mass analyzer.

6. A method of claim 1, further comprising:
   performing a mass spectral analysis on a sample comprising one or more microorganisms.

7. A method of claim 1, further comprising:
   identifying molecular weights of proteins in a mass spectrum of said sample.

8. A method of claim 1, wherein said sample comprises at least two different species of microorganisms.

9. A method of claim 1, wherein the sequence database comprises NCBI/SwissProt/EMBL database.

10. A method of claim 1, further comprising chemical or enzymatic digestion of a protein in said sample.

11. A method of claim 1, wherein said sequence database comprises nucleotide or protein sequence information that is converted into molecular weight information.

12. A method of claim 1, wherein the database searching consists of searching a database for a plurality of intact, undigested proteins.

13. A method of claim 1, further comprising inputting said molecular weights obtained from said mass spectrum.

* * * * *

UNITED STATES PATENT AND TRADEMARK OFFICE
CERTIFICATE OF CORRECTION

PATENT NO. : 7,020,559 B1 Page 1 of 1
APPLICATION NO. : 09/856044
DATED : March 28, 2006
INVENTOR(S) : Plamen A. Demirev It is certified that error appears in the above-identified patent and that said Letters Patent is hereby corrected as shown below:

On the front page, Item (75) Inventors: line 2, reads "Fenseleau" should read -- Fenselau --

Column 17, line 16, reads "have been fragmented" should read -- have not been fragmented --

Column 17, line 17, reads "orenzymatic" should read -- or enzymatic --

Signed and Sealed this

Fifteenth Day of May, 2007

JON W. DUDAS
*Director of the United States Patent and Trademark Office*